(12) United States Patent
Griess et al.

(10) Patent No.: US 7,398,698 B2
(45) Date of Patent: Jul. 15, 2008

(54) SMART REPAIR PATCH AND ASSOCIATED METHOD

(75) Inventors: Kenneth H. Griess, Kent, WA (US); Gary E. Georgeson, Federal Way, WA (US)

(73) Assignee: The Boeing Company, Chicago, IL (US)

( * ) Notice: Subject to any disclaimer, the term of this patent is extended or adjusted under 35 U.S.C. 154(b) by 131 days.

(21) Appl. No.: 11/266,499

(22) Filed: Nov. 3, 2005

(65) Prior Publication Data

US 2007/0100582 A1 May 3, 2007

(51) Int. Cl.
*G01N 29/04* (2006.01)
*G01N 3/00* (2006.01)

(52) U.S. Cl. .......................... 73/801; 73/12.08; 73/802; 702/36

(58) Field of Classification Search ................ 73/12.08, 73/801, 802; 702/34–36
See application file for complete search history.

(56) References Cited

U.S. PATENT DOCUMENTS

| | | | |
|---|---|---|---|
| 4,058,003 A | 11/1977 | Macovski | |
| 4,838,085 A * | 6/1989 | Pellerin et al. | ................ 73/597 |
| 5,073,814 A | 12/1991 | Cole, Jr. et al. | |
| 5,091,893 A | 2/1992 | Smith et al. | |
| 5,165,270 A | 11/1992 | Sansalone et al. | |
| 5,614,670 A | 3/1997 | Nazarian et al. | |
| 5,680,863 A | 10/1997 | Hossack et al. | |
| 5,735,282 A | 4/1998 | Hossack | |
| 5,814,731 A | 9/1998 | Alexander et al. | |
| 5,869,189 A | 2/1999 | Hagood, IV et al. | |
| 5,983,701 A | 11/1999 | Hassani et al. | |
| 6,370,964 B1 * | 4/2002 | Chang et al. | ........... 73/862.046 |
| 6,424,597 B1 | 7/2002 | Bolomey et al. | |
| 6,476,541 B1 | 11/2002 | Smith et al. | |
| 6,586,702 B2 | 7/2003 | Wiener-Avnear et al. | |

(Continued)

FOREIGN PATENT DOCUMENTS

| | | |
|---|---|---|
| EP | 1 484 608 A2 | 12/2004 |
| WO | WO 94/13411 A1 | 6/1994 |

OTHER PUBLICATIONS

C. Wang, J.H. Park, F. Chang. "Impact damage identification of composite structures with built-in piezoelectric sensor/actuator networks" DTIC (2003) Accessed online on Dec. 20, 2007 at <http://andle.dtic.mil/100.2/ADA412408>.*

(Continued)

*Primary Examiner*—Edward Lefkowitz
*Assistant Examiner*—Punam Patel
(74) *Attorney, Agent, or Firm*—Alston & Bird LLP (57) ABSTRACT

A system and method for identifying defects in a repair patch applied to a structure are provided. The system includes a sheet of material configured to be attached to the structure, and a mechanism operable to generate stress waves within and along the sheet of material. The system also includes a plurality of non-destructive sensors carried by the sheet of material. Each sensor is capable of detecting the stress waves. The system further includes a data acquisition system capable of communicating with the sensors such that the data acquisition system is also capable of generating information indicative of at least a portion of the sheet of material based on the data detected by the sensors.

21 Claims, 5 Drawing Sheets

U.S. PATENT DOCUMENTS

| | | | |
|---|---|---|---|
| 6,598,485 | B1 | 7/2003 | Lin et al. |
| 6,656,124 | B2 | 12/2003 | Flesch et al. |
| 6,798,717 | B2 | 9/2004 | Wiener-Avnear et al. |
| 6,799,126 | B1* | 9/2004 | Ratcliffe et al. ............... 702/56 |
| 6,822,374 | B1 | 11/2004 | Smith et al. |
| 2002/0190729 | A1* | 12/2002 | Wilson ....................... 324/663 |
| 2003/0094031 | A1 | 5/2003 | Huang et al. |
| 2004/0123665 | A1 | 7/2004 | Blodgett et al. |
| 2005/0068041 | A1* | 3/2005 | Kress et al. ................. 324/527 |
| 2007/0017297 | A1* | 1/2007 | Georgeson et al. ........... 73/801 |

OTHER PUBLICATIONS

The Impact-Echo Technology; *Impact-Echo Instruments, LLC*; 2 pages, available at http://www.impact-echo.com/pages/technology.html; downloaded Jul. 5, 2005.

Mary J. Sansalone and William B. Streett; The Impact-Echo Method; *NDTnet*, Feb. 1998, vol. 3, No. 2; 9 pages available at http://www.ndt.net/article/0298/streett/streett.htm.

Impact-Echo Testing; *Whitlock, Dalrymple, Poston & Associates*; I page, available at http://www.wdpa.com/impactecho.html; downloaded Jan. 5, 2005.

Electrical and Electronic Engineering, NDT, Nondestructive Testing, NDE, Nondestruti. . . ; *HD Laboratories, Inc.*; 2 pages, available at http://www.hdlabs.com; downloaded Mar. 25, 2005.

N.J. Carino; The Impact-Echo Method: An Overview; *National Institute of Standards and Technology*; pp. 1-18 (2001).

Flexible Ultrasonic Arrays; *HD Laboratories, Inc.*; 3 pages, available at http://www.hdlabs.com/NDT/FlexibleArrays/flexiblearrays.htm; downloaded Mar. 25, 2005.

Kress K-P et al.; "Smart Wide-Area Imaging Sensor System (SWISS)" Proceedings of the Spie, Spie , Bellingham, VA, US; vol. 4332, Mar. 5, 2001; pp. 490-496, XP008014768; ISSN: 0277-786X.

* cited by examiner

SMART REPAIR PATCH AND ASSOCIATED METHOD

BACKGROUND OF THE INVENTION

1) Field of the Invention

The present invention relates to smart patches and, more particularly, to a smart repair patch for monitoring the integrity of the repair patch.

2) Description of Related Art

Materials and structures employed in the aerospace industry and elsewhere may periodically require repair for in-service damage. Rapid inspection and repair of aircraft or ground vehicles are important for military and commercial applications in order to decrease down time. Temporary patch repairs of a metallic or composite structure are sometimes utilized to enable continuing use of the vehicle, such as an aircraft, until a permanent repair may be made. Temporary patches cost less than permanent repairs and can be installed very rapidly. In addition, temporary patches reduce down time and provide flexibility for utilizing the best schedule and cost options available.

However, confidence in the quality of the temporary repairs has decreased. In particular, temporary patches can detach from the structure without warning if the patches are not checked regularly. However, inspection of temporary patches tends to be costly in light of the time and labor required to perform the inspection. For example, a temporary patch inspection program may require that the patches be inspected after every flight for the first week, then every day for a week, and then weekly for a period of time. To avoid inspection costs, the user may apply a more costly temporary repair patch, choose a limited time window of temporary patch use, or choose to proceed with an immediate permanent repair; all of which decrease available repair options. Furthermore, conventional methods for inspecting temporary repair patches (e.g., tap testing) can be subjective and not provide quantitative data for time-based comparison. Various alternatives to inspect temporary repair patches employ electronic equipment which may be expensive, time-consuming, and require trained experts in order to use.

Repair patches have been developed that generally acquire data indicative of a structure and the repair patch itself. For example, U.S. Pat. No. 5,553,504 to Lyons et al. discloses an instrumented patch for repair of a structure. In particular, Lyons discloses an apparatus that includes a plurality of strain sensors integrally formed with a patch to be fixed to an area on the surface of a structure. The sensors monitor changes in the strain field in the patch-covered area for detecting crack formation and detection, as well as the structural integrity of the patch. Namely, anomalies, such as tears or holes in the patch, or partial detachment of the patch from the structure, can be detected by measuring changes in the strain field in the region of the patch-covered area with the strain sensors. There is a need for an improved system that includes a repair patch that is capable of not only repairing a structure, but also performing NDI on the repair patch itself.

It would therefore be advantageous to provide a system that is capable of both repairing and monitoring the integrity of the repair patch. In addition, it would be advantageous to provide a system that is capable of inspecting the repair patch effectively and efficiently. Furthermore, it would be advantageous to provide a system that is economical to manufacture and use.

BRIEF SUMMARY OF THE INVENTION

Embodiments of the invention address the above needs and achieve other advantages by providing a system to inspect a repair patch applied to a structure for defects. In particular, the system is capable of inspecting a repair patch that has been attached to a structure. The system incorporates a sheet of material having several sensors secured thereon. A mechanism is used to generate stress waves within and along a surface of the sheet of material. The sensors communicate with a data acquisition system to generate information that identifies defects within the sheet of material. Employing an impact-echo method, for example, allows the inspection system to inspect composite and metallic structures more rapidly and at a lower cost than conventional inspection techniques.

In one embodiment of the present invention, a system for identifying defects in a repair patch applied to a structure is provided. The system includes a sheet of material configured to be attached to the structure, and a mechanism operable to generate stress waves within and along the sheet of material. The system also includes a plurality of non-destructive sensors (e.g., piezo-electric sensors) carried by the sheet of material. Each sensor is capable of detecting the stress waves. The system further includes a data acquisition system that is capable of communicating with the sensors such that the data acquisition system is also capable of generating information indicative of at least a portion of the sheet of material based on the data detected by the sensors.

In various aspects of the system, the data acquisition system is capable of generating information indicative of an adhesion of the sheet of material to the structure based on the data detected by the sensors. In addition, the data acquisition system may generate information indicative of a defect in the sheet of material based on the data detected by the sensors. The mechanism could also generate stress waves within and along a surface of the structure such that the data acquisition system may generate information indicative of a defect in the structure based on the data detected by the sensors.

In additional aspects of the system, the sheet of material is configured to be temporarily attached to the structure and could be a pre-cured composite material. The sensors could be arranged about the periphery of the sheet of material, such as in a ring. The mechanism for generating the stress waves could take many forms such as a tapper, a tapper having a spring-loaded bar, one or more clickers, a hammer, or a pulser card. The mechanism may generate the stress waves at approximately a center of the sheet of material in one embodiment.

Another aspect of the present invention provides a method for identifying defects in a repair patch applied to a structure. The method includes attaching a sheet of material carrying a plurality of non-destructive inspection sensors to the structure, and generating stress waves within and along a surface of the sheet of material. The method also includes detecting the stress waves with the sensors, and deriving information from the stress waves that is indicative of at least a portion of the sheet of material.

In aspects of the method, the deriving step includes deriving information indicative of a defect in the sheet of material. The generating step may include initiating stress waves approximately at the center of sheet of material. In addition, the generating step could include generating stress waves within and along a surface of the structure such that information may be derived from the stress waves that is indicative of at least a portion of the structure. Moreover, the method may further include communicating the data acquired by the sensors to a data acquisition system and creating an image of at least a portion of the sheet of material with the data acquisition system based on the data detected by the sensors.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

The present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Figure 1:
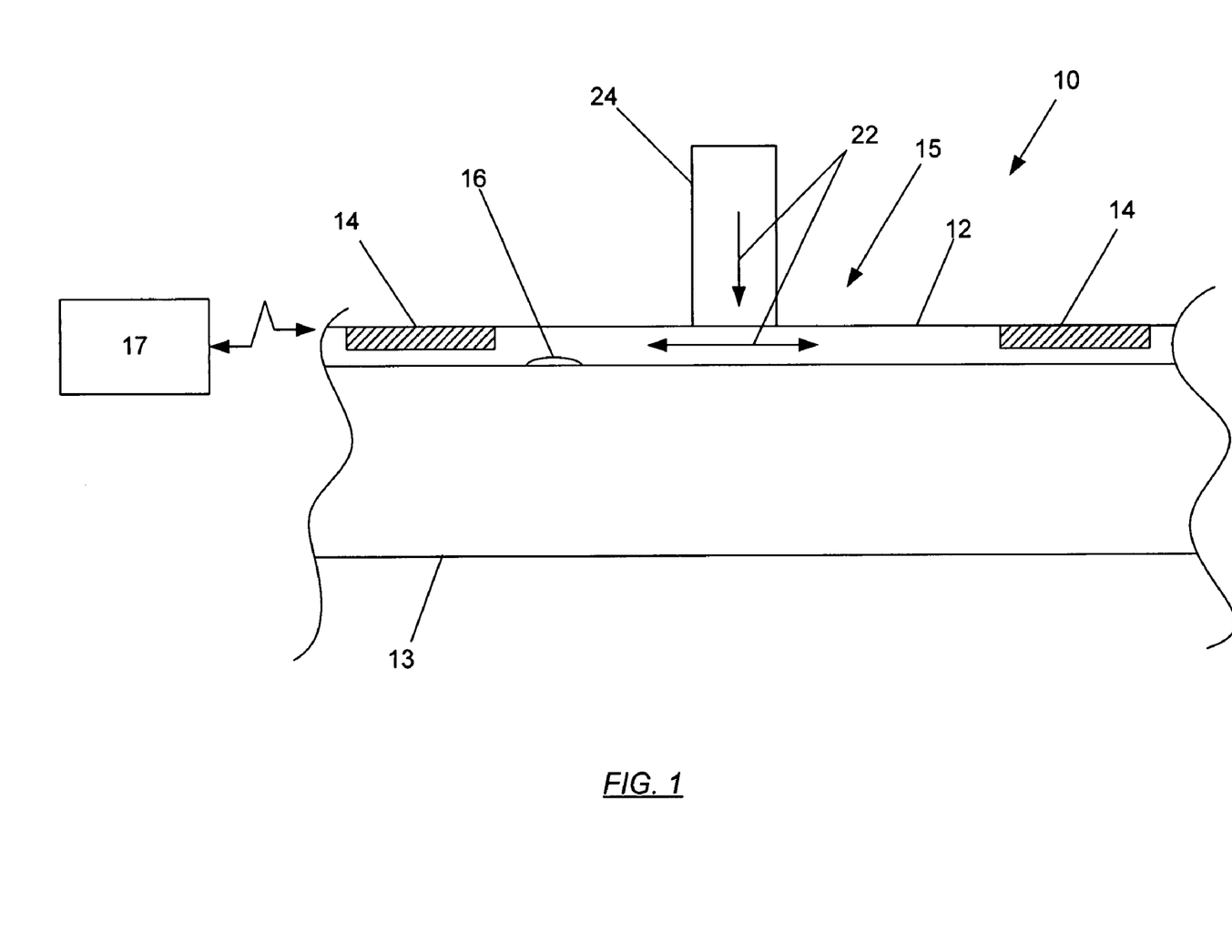
FIG. 1 is a cross-sectional view of an inspection system according to one embodiment of the present invention.
Figure 2A:
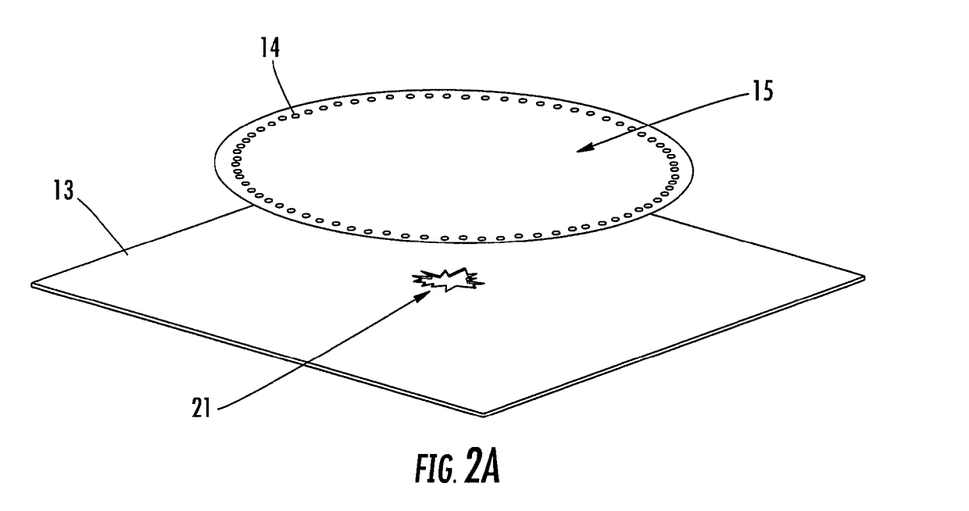
FIGS. 2A and 2B are perspective views of a repair patch applied to a structure having a defect according to one embodiment of the present invention.
Figure 2B:
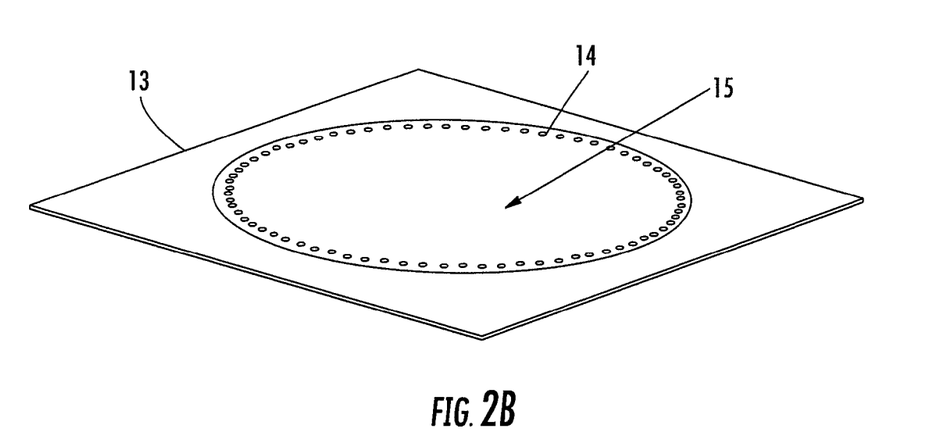

Referring now to the drawings and, in particular to FIGS. 1 and 2A-2B, there is shown an inspection system 10. The inspection system 10 includes a repair patch 15 that is attached to a structure 13 for repairing a defect in a structure. The repair patch could be employed to repair or detect any number of defects 21 within or along a surface of the structure 13 such as cracks, disbonds, discontinuities, voids, or porosity, which could adversely affect the performance of the structure (see FIGS. 2A-2B). The repair patch 15 could be a temporary patch that is applied until a permanent repair can be made, or the repair patch could be permanent. In addition, the repair patch 15 includes a sheet of material 12 having a plurality of non-destructive sensors 14 arranged about the sheet. The sensors 14 are capable of detecting data indicative of a defect 16 in a repair patch 15. As will be explained in greater detail below, a mechanism 24 is used to generate stress waves 22 along and within the sheet of material 12 such that the sensors 14 are capable of detecting the stress waves. The sensors 14 are typically in communication with a data acquisition system 17 to generate various images of a portion of the sheet of material 12 based on data collected by the sensors.

Figure 3:
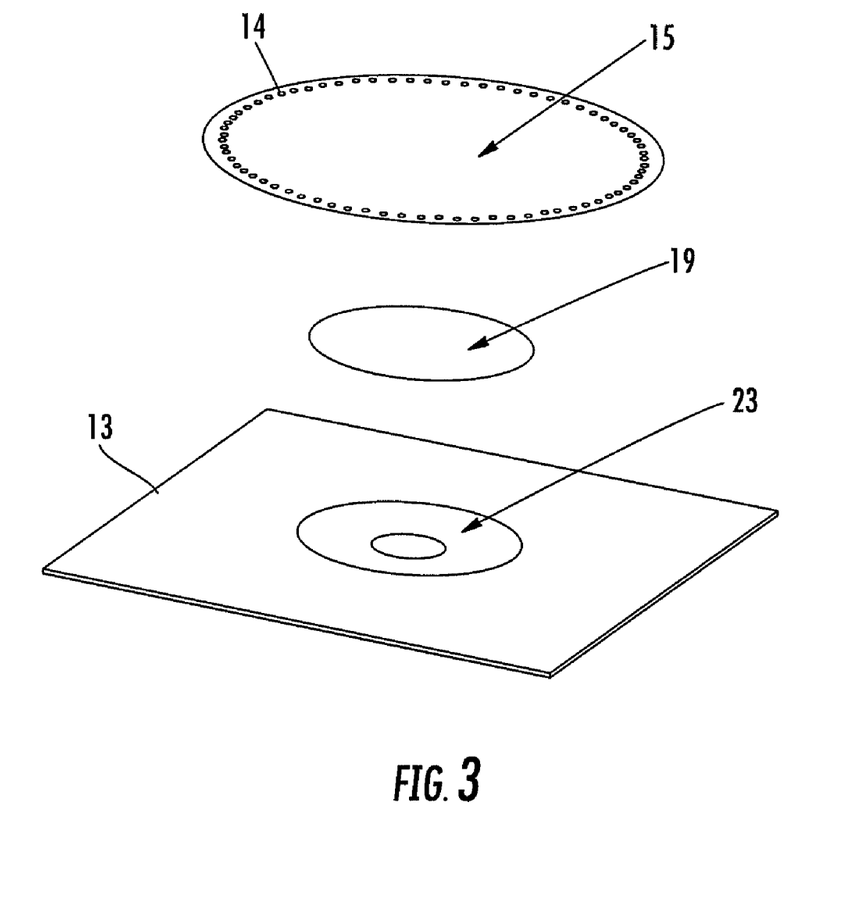
FIG. 3 is a perspective view of a repair patch applied to a structure having a permanent patch attached thereto according to one embodiment of the present invention.

The inspection system 10 could be used to inspect any number of repair patches 15 and structures 13 in a variety of industries where detection of flaws or defects in the repair patch is required, such as in the aircraft, automotive, or construction industries. The sensors 14 are capable of detecting any number of defects within or along the surface of the repair patch and/or structure. For example, the sensors 14 could detect disbonds or delaminations associated with the repair patch 15 to determine whether the repair patch is adequately adhered to the structure 13. Furthermore, as shown in FIG. 3, the repair patch 15 could be applied over a permanent repair 19 to monitor the integrity of the permanent repair. For example, the defect in the structure may be removed using a conventional scarf repair 23, although other techniques known to those of ordinary skill in the art could be employed to repair defects in the structure 13.

The terms "repair patch" and "structure" are not meant to be limiting, as the repair patch 15 could be used to repair any number of parts or structures 13 of different shapes and sizes, such as machined forgings, castings, or composite panels or parts. Further, the repair patch 15 and structure could be formed of any number of materials. For example, the repair patch 15 and structure 13 could be formed of metallic material, such as aluminum, or composite material, such as graphite-epoxy. In one embodiment, for example, the repair patch 15 and structure 13 are each generally formed from a thin material that is used, for instance, as aircraft skin. For example, the structure 13 could be an aircraft, such as the Boeing 787 Dreamliner, where a substantial portion of the aircraft structure is a composite material (e.g., the fuselage and wings).

The sheet of material 12 may be the same or a different type of material as the structure 13 to be repaired. For example, the sheet of material 12 could be a pre-cured composite material, such as graphite-epoxy, that is attached to an aluminum structure 13. In addition, the sheet of material 12 may be flexible and pliable to allow the sheet to be manipulated to conform to a variety of surface contours for inspection, as well as maintain intimate contact with the underlying structure 13. However, the sheet of material 12 could also be rigid and provide support to the area of the structure 13 including the defect. The sheet of material 12 could be various dimensions to repair different sizes of defects. For example, the sheet of material 12 could be circular, as shown in FIG. 2A, and extend about and beyond the defect in the structure 13. U.S. Pat. No. 5,034,254, entitled "Blind Side Panel Repair Patch," which is assigned to the present assignee and incorporated herein by reference, provides an exemplary description of a repair patch and the application of the same to a structure.

Current paths to and from each sensor 14 are incorporated (e.g., through some form of metallic deposition, etching, or bonding) or attached (e.g., via wires) to the sheet of material 12. Each of the sensors 14 may be attached to the current paths of this conductive network so that the sensors may communicate with the data acquisition system 17. The network serves to aggregate signals from sensors 14 such that a single cable connects the network to the data acquisition system 17 in a wireline embodiment. Yet, separate communication wires or cables may extend between each respective sensor 14 and the data acquisition system 17 such that the network is not required. However, not including a conductive network and, instead, including several sensors 14 on a single sheet of material 12 may be undesirable as several wires or cables extending to the data acquisition system 17 may become difficult to manage or maneuver. Moreover, in one embodiment of the present invention, the sensors 14 could communicate wirelessly with data acquisition system 17, as shown in FIG. 1, such as by employing radiofrequency transmitters to transmit data to the data acquisition system 17. For instance, see U.S. patent application Ser. No. 11/266,459, entitled "Structural Assessment and Monitoring System and Associated Method," which is filed concurrently herewith, assigned to the present assignee, and incorporated herein by reference. Furthermore, in an additional embodiment of the present invention, the sheet of material 12 may include one or more power sources. For example, the sheet of material 12 could include one or more thin, flexible batteries, such as those manufactured by Power Paper®, to power the sensors 14 such that the sensors may detect and collect data indicative of the sheet of material in a passive mode without requiring an external power source. Thereafter, the data detected by the sensors 14 could be communicated to the data acquisition system 17, as described above.

Each of the non-destructive sensors 14 could be any suitable sensor capable of detecting data indicative of the sheet of material 12. Each sensor 14 is typically a non-destructive sensor, such that the sensor is capable of inspecting the sheet of material 12 without harming the sheet of material or requiring disassembly of the sheet of material from the structure. In the embodiment of the inspection system 10 shown in FIG. 1, each sensor 14 is an ultrasonic sensor, such as a piezo-electric sensor. The sensors 14 may be carried by the sheet of material 12 using various techniques. For example, the sensors 14 could be integral to, or embedded within, the sheet of material 12, or the sensors could be attached or otherwise secured to the sheet of material such as, for example, by adhesives.

The sensors 14 are arranged on the sheet of material 12 in a variety of configurations. For example, FIG. 2A illustrates by the darker elements that the sensors 14 are arranged circumferentially about the periphery of the sheet of material 12. However, it is understood that the sensors 14 may be arranged in any number of configurations on the sheet of material 12. As the number of sensors 14 increases, or the distance between the sensors decreases, the smaller the defect that may be detected. Therefore, the number and/or arrangement of the sensors 14 may be varied depending on the size of the defect to be detected and to achieve a particular resolution of the inspection image. The sensors 14 of the inspection system 10 may be reusable or disposable.

The system 10 of the present invention, according to one embodiment, employs an impact-echo technique to generate stress waves within and along the surface of the sheet of material 12. See U.S. patent application Ser. No. 11/186,021, entitled "Non-Destructive Inspection System and Associated Method," which is assigned to the present assignee and incorporated herein by reference, for a detailed discussion of the impact-echo technique.

An impact mechanism 24 is used to generate stress waves 22 within and along the surface of the sheet of material 12 to detect defects 16, as shown in FIG. 1. For example, the mechanism 24 could be a tapper, a tapper having a spring-loaded bar, one or more clickers (e.g., a center punch), or a hammer. Generally, the amount of force applied by the impact mechanism 24 is known so that a consistent force is applied to the sheet of material 12. The impact mechanism 24 could be manually controlled by an inspector or automatically performed without human intervention. Moreover, a piezo-electric transducer activated by a high voltage pulse (i.e., a pulser) could be employed to generate stress waves. Thus, there could be various mechanisms used to generate stress waves 22 for a particular inspection system 10. The system 10 could utilize a single impact mechanism 24, but the inspection system 10 could include one or more impact mechanisms, where multiple impact mechanisms could be activated simultaneously or sequentially. In addition, the impact mechanism 24 may be independent or separate from the sheet of material 12, or the impact mechanism could be integrated or built into the sheet of material. A simple hand-held tap hammer could be used as an impact mechanism 24 if only time-of-flight information is used since the time of stress wave 22 travel will not generally depend upon the level of impact. However, proper selection of impact duration and frequency content (by selecting a particular impact ball, for example) will determine how well the stress wave interacts with the interior damage structure.

Frequency response, time-of-flight, or amplitude of the stress waves 22 can be used, separately, or in combination to characterize and identify defects within the repair patch 15. Thus, defects may not only be identified and located, but the defect could be characterized, such as by determining the depth of damage or the percent loss of adhesion between the sheet of material 12 and the structure 13. Typically, the more information utilized, the better the characterization and identification of the defects. Furthermore, the impact mechanism 24 could also generate stress waves 22 within and along the structure 13 proximate to the repair patch 15. The sensors 14 could be configured to detect the stress waves 22 traveling through the structure 13 and communicate with the data acquisition system 17 such that defects located in the structure may also be located and characterized. The stress waves 22 traveling through each of the repair patch 15 and structure 13 could be generated by a single impact to the repair patch, and the sensors 14 may detect data associated with the stress waves for the repair patch and structure concurrently or at separate times.

Figure 4:
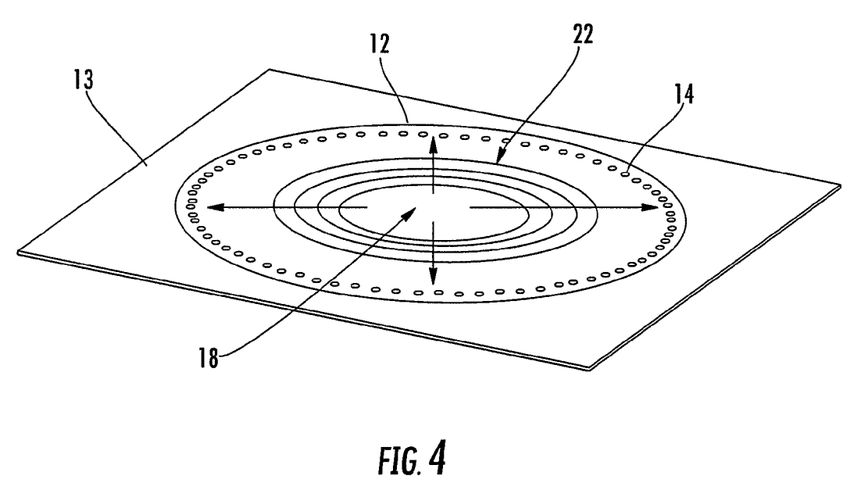
FIGS. 4 and 5 are perspective views of a repair patch illustrating stress waves traveling through the repair patch according to one embodiment of the present invention.
Figure 5:
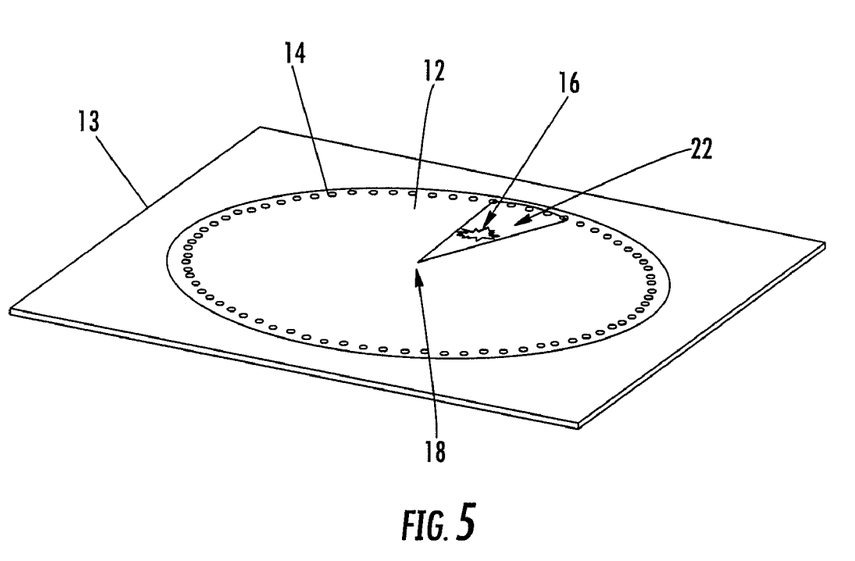

The location of impact is typically known so that a proper correlation may be made between the force applied and the distance between the impact and each of the sensors 14, which is explained in further detail below. FIGS. 4 and 5 show the impact locations 18 in approximately the center of the sheet of material 12. However, the location of applying the impact on the sheet of material 12 may vary. For instance, the impact locations could be about the periphery of the sheet of material 12 or at random locations.

Impact locations 18 define where the stress waves 22 are initiated, and the number and location of which should be sufficient to produce enough impact-to-sensor paths to make a sufficient image for detecting potential defects. The sheet of material 12 can have one or more precisely located impact locations, as described above. However, precise locations may be unnecessary, since the location of impact can be determined through triangulation, such as that shown in FIG. 4. If the speed or time of travel of a stress wave 22 through the repair patch 15 without defects is known, the relative time it takes for the stress wave to reach individual sensors in the structure will define the impact location. This assumes that the edge of the sheet of material 12 where triangulation is being used is over flawless material since a near-by defect will generally affect the triangulation results because it can change the speed of the stress wave 22. Selecting precise locations of impact typically simplifies the math and computer calculations required by the data acquisition system 17, while arbitrary impact locations typically require triangulation and more complicated reconstruction software. It is understood that one skilled in the art could readily design algorithms to analyze stress waves 22 and identify and/or characterize defects in the repair patch 15 since these methods are generally known for this type of testing. The software may be made to be selectable, so that various impact options (e.g., impact location) are available.

In addition to the time of travel, the stress wave 22 amplitude data collected at each sensor 14 could provide valuable information. For example, a damaged area might not permit plate waves (i.e., Lamb waves) to pass through the repair patch 15 or may dramatically reduce their amplitude. If the locations of impact 18 are precisely known, the amplitudes between impact can be normalized by comparing sensor data where there is a defect-free area of equally spaced sensors 14. Those skilled in the art will recognize techniques to compare amplitudes to demonstrate that a defect is located between the site of impact 18 and the sensors 14. In general, either precise location or level of impact is desired. When both the location and level of impact is provided, the quality of the level of defect detection is increased (since there is some redundancy), which typically provides simplification of the data analysis.

An inspector could observe the image formation in a batch process or in real time as he or she initiates impacts at one or more locations on the sheet of material 12. As the impact mechanism 24 applies impact at more locations, the better the image will generally become, since the software would generally be designed to be able to add the results of new data into the forming image. The inspector could even initiate additional impact locations 18 in one area or another to complete an image where data is missing or otherwise incomplete.

When the impact mechanism 24 generates one or more stress waves 22 on the surface of the structure 13 and within the sheet of material 12, each sensor 14 will receive a signal at a particular time and of a particular amplitude. Depending on the type of material and thickness of the structure 13, the speed of the stress waves 22 may be determined when the impact mechanism 24 applies a consistent force to the sheet of material 12. Since the speed can be known or determined for a particular material and thickness, the path between impact 18 and sensor 14 can be analyzed for damage. Thinning of the structure 13 due to disbanding, delamination, or corrosion thinning will affect the velocity of the plate wave. Furthermore, defects or localized damage will obstruct the stress wave path. Since the sensor 14 locations are known, defects or damage location and size can be mapped onto a grid that represents their locations on the sheet of material 12.

FIGS. 4 and 5 illustrate that the impact mechanism 24 generates stress waves 22 at approximately at the center of the sheet of material 12. The stress waves 22 propagate radially and outwardly across the surface of the sheet of material 12. Thus, a single impact on the sheet of material 12 identifies and bounds the defect 16. Time of flight between the impact location 18 and respective sensors 14 along with characteristics of the stress waves 22 may be used to quantify the defect 16.

The data acquisition system 17 typically includes a processor or similar computing device operating under the control of imaging software so that any defects in the repair patch 15 may be presented on a display. It is possible to incorporate the data acquisition system 17 without a display and to instead provide a printout of the image scan, or to utilize any other technique for viewing the scan and location data. The processor could be embodied by a computer such as a desktop, laptop, or portable processing device capable of processing the data generated by the sensors 14 and creating an image, such as a B-scan or C-scan, of the scanned data that is shown on a display such as a monitor or other viewing device. The data acquisition system 17 is capable of generating images indicative of a defect and may also allow a user to store and edit previously created images. Therefore, a permanent record of the images may be kept for future use or record keeping. However, it is understood that the data acquisition system 17 need not generate images, as the data acquisition system could mathematically collect and analyze data and generate, for example, time, amplitude, etc., that a technician could use to characterize a defect based on the data.

Each sensor 14 is typically in communication with the data acquisition system 17, either directly or via the conductive network, to process the data accumulated by the sensors and to display the processed data. In many cases, communication cable(s) transmit data between the sheet of material 12, sensors 14, and the data acquisition system 17. For instance, a communication cable could be used that is capable of transmitting data acquired by the sensors 14 to the data acquisition system 17. The communication cable could be linked to a conductive network, as described above, to facilitate communication between several sensors 14 and the data acquisition system 17. In other embodiments, the data may be transmitted between the sensors 14 and the data acquisition system 17 via wireless communications (e.g., radiofrequency), or at least between the conductive network and the data acquisition system. The sensors 14 may be directly connected to the processor, or indirectly connected, such as via a network. In further embodiments of the present invention the data acquisition system 17 may be located proximate to the sensors 14, such that remote connections between the sensor and data acquisition system are not necessary.

Thus, the present invention provides several advantages. The inspection system 10 may provide image-based ultrasonic array data at a lower cost than conventional inspection techniques. Furthermore, the inspection system 10 may collect data more rapidly than most conventional scanning systems. The inspection system 10 may also provide quantitative image-based data that conventional hand-held ultrasonic testing and tap testing cannot generally provide. The inspection system 10 also enables rapid inspection of composite and metallic repair patches 15. In addition, the inspection system 10 is capable of determining the integrity of the repair patch 15, thus providing information as to whether remedial action needs to be taken, such as a permanent repair.

Many modifications and other embodiments of the invention set forth herein will come to mind to one skilled in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A system for identifying defects in a repair patch applied to a structure comprising:
   a sheet of material configured to be attached to the structure;
   a mechanism operable to generate stress waves within and along the sheet of material;
   a plurality of non-destructive sensors carried by the sheet of material, each sensor capable of detecting the stress waves, wherein each of the plurality of sensors is positioned proximate to an outer periphery of the sheet of material such that the plurality of sensors are not located on an inner portion of the sheet of material, and wherein the impact mechanism is operable to generate stress waves on the inner portion of the sheet of material; and
   a data acquisition system capable of communicating with the sensors such that the data acquisition system is capable of generating information indicative of a defect in the sheet of material based on the data detected by the sensors.

2. The system according to claim 1, wherein the data acquisition system is capable of generating information indicative of an adhesion of the sheet of material to the structure based on the data detected by the sensors.

3. The system according to claim 1, wherein the mechanism is capable of generating stress waves within and along a surface of the structure.

4. The system according to claim 3, wherein the data acquisition system is capable of generating information indicative of a defect in the structure based on the data detected by the sensors.

5. The system according to claim 1, wherein the sheet of material is configured to be temporarily attached to the structure.

6. The system according to claim 1, wherein the sensors comprise piezo-electric sensors.

7. The system according to claim 1, wherein the sensors are arranged in a circular configuration about the outer periphery of the sheet of material.

8. The system according to claim 1, wherein the mechanism comprises a tapper, a tapper having a spring-loaded bar, one or more clickers, a hammer, or a pulser card.

9. The system according to claim 1, wherein the mechanism is capable of generating the stress waves at approximately a center of the sheet of material.

10. The system according to claim 1, wherein the sheet of material comprises a pre-cured composite material.

11. A patch for repairing a structure comprising:
a flexible sheet of material capable of being temporarily attached to the structure, the material from which the flexible sheet is comprised being configured to repair a defect in the structure; and
a plurality of non-destructive sensors carried by the sheet of material, wherein each of the plurality of sensors is positioned proximate to an outer periphery of the sheet of material such that the plurality of sensors are not located on an inner portion of the sheet of material, and wherein each of the sensors is capable of detecting stress waves that are generated on the inner portion of the sheet of material and that travel within and along the sheet of material.

12. The patch according to claim 11, wherein the sensors are arranged in a circular configuration about the outer periphery of the sheet of material.

13. The patch according to claim 11, wherein the sensors comprise piezo-electric sensors.

14. The patch according to claim 11, wherein the sheet of material comprises a pre-cured composite material.

15. The patch according to claim 11, further comprising at least one power source for powering the sensors.

16. A method for identifying defects in a repair patch applied to a structure comprising:
attaching a sheet of material carrying a plurality of non-destructive inspection sensors to the structure, wherein each of the plurality of sensors is positioned proximate to an outer periphery of the sheet of material such that the plurality of sensors are not located on an inner portion of the sheet of material;
generating stress waves on the inner portion of the sheet of material such that the stress waves travel within and along a surface of the sheet of material to the outer periphery of the sheet of material;
detecting the stress waves with the sensors; and
deriving information from the stress waves that is indicative of a defect in the sheet of material.

17. The method according to claim 16, wherein generating comprises initiating stress waves approximately at the center of the sheet of material.

18. The method according to claim 16, wherein generating comprises generating stress waves within and along a surface of the structure.

19. The method according to claim 18, wherein deriving comprises deriving information from the stress waves that is indicative of at least a portion of the structure.

20. The method according to claim 16, further comprising communicating the data acquired by the sensors to a data acquisition system and creating an image of at least a portion of the sheet of material with the data acquisition system based on the data detected by the sensors.

21. A patch for repairing a structure comprising:
a flexible sheet of material capable of being attached to the structure, wherein the sheet of material comprises a pre-cured composite material configured to repair a defect in the structure; and
a plurality of non-destructive sensors carried by the sheet of material, wherein each of the plurality of sensors is positioned proximate to an outer periphery of the sheet of material such that the plurality of sensors are not located on an inner portion of the sheet of material, and wherein each of the sensors is capable of detecting stress waves that are generated on the inner portion of the sheet of material and that travel within and along the sheet of material.

* * * * *